(12) United States Patent
Timken et al.

(10) Patent No.: US 10,059,639 B2
(45) Date of Patent: Aug. 28, 2018

(54) ALKYLATION OF REFINERY PENTENES WITH ISOBUTANE

(71) Applicant: Chevron U.S.A. Inc., San Ramon, CA (US)

(72) Inventors: Hye-Kyung Cho Timken, Albany, CA (US); Bong-Kyu Chang, Novato, CA (US); Sven Ivar Hommeltoft, Pleasant Hill, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 15/255,271

(22) Filed: Sep. 2, 2016

(65) Prior Publication Data
US 2018/0065899 A1 Mar. 8, 2018

(51) Int. Cl.
| | |
|---|---|
| C07C 2/56 | (2006.01) |
| C07C 2/58 | (2006.01) |
| B01J 31/02 | (2006.01) |
| C10L 1/06 | (2006.01) |
| C10G 29/20 | (2006.01) |
| C10G 17/02 | (2006.01) |

(52) U.S. Cl.
CPC ............ *C07C 2/58* (2013.01); *B01J 31/0284* (2013.01); *C10G 17/02* (2013.01); *C10G 29/205* (2013.01); *C10L 1/06* (2013.01); *B01J 2231/32* (2013.01); *C07C 2531/02* (2013.01); *C10G 2300/1088* (2013.01); *C10G 2400/02* (2013.01); *C10L 2270/023* (2013.01)

(58) Field of Classification Search
CPC ...................................... C07C 2/58
USPC ............................ 585/14, 16, 709
See application file for complete search history.

(56) References Cited

U.S. PATENT DOCUMENTS

| | | | |
|---|---|---|---|
| 3,865,894 A | 2/1975 | Kirsch et al. | |
| 5,157,196 A | 10/1992 | Crossland et al. | |
| 5,382,744 A | 1/1995 | Abbott et al. | |
| 5,648,586 A * | 7/1997 | Sampath | C07C 2/62 585/300 |
| 7,988,747 B2 | 8/2011 | Lacheen et al. | |
| 8,921,636 B2 | 12/2014 | Cleverdon et al. | |
| 2009/0107032 A1 | 4/2009 | Lacheen et al. | |
| 2011/0092753 A1 | 4/2011 | Zhan et al. | |
| 2011/0130602 A1* | 6/2011 | Hommeltoft | C07C 2/58 585/312 |
| 2011/0144399 A1 | 6/2011 | Elomari et al. | |
| 2011/0155632 A1 | 6/2011 | Timken et al. | |
| 2011/0282114 A1 | 11/2011 | Luo et al. | |
| 2013/0066121 A1* | 3/2013 | Zhan | C07C 2/60 585/251 |
| 2014/0179977 A1 | 6/2014 | Timken et al. | |

FOREIGN PATENT DOCUMENTS

WO    9414734 A1    7/1994

OTHER PUBLICATIONS

Kranz, K. "Alkylation Chemistry" (2003); pp. 1, 18, and 23.*
Stratco report, published in 1999 by Randall Peterson, David Graves, Ken Kranz and David Buckler.
PCT International Search Report and Written Opinion, International Application No. PCT/US2017/042517, dated Dec. 19, 2017, pp. 1-19.

* cited by examiner

*Primary Examiner* — Philip Y Louie
*Assistant Examiner* — Aaron W Pierpont
(74) *Attorney, Agent, or Firm* — Susan M. Abernathy

(57) ABSTRACT

A process, comprising: providing an olefin feed comprising pentenes, butenes, and isopentane; and alkylating the olefin feed with isobutane using an acidic ionic liquid catalyst; wherein less than 5 mol % of C5 olefins in the olefin feed are converted to isopentane, and the alkylate gasoline has defined final boiling points and high RONs. A process comprising: alkylating an olefin feed comprising pentenes and isopentane, with isobutane using an acidic ionic liquid catalyst; wherein less than 5 mol % of C5 olefins in the olefin feed are converted to isopentane; and wherein an n-pentane product yield is low. An alkylate gasoline, comprising less than 0.1 wt % olefins and aromatics, less than 1.8 wt % C12+hydrocarbons, and greater than 60 wt % combined C8 and C9 hydrocarbons, wherein the trimethylpentane in the C8 hydrocarbons and the trimethylhexane in the C9 hydrocarbons are defined.

19 Claims, No Drawings

ALKYLATION OF REFINERY PENTENES WITH ISOBUTANE

TECHNICAL FIELD

This application is directed to high quality alkylate gasoline and processes to produce high quality alkylate gasoline from olefin feeds comprising pentenes, while producing very low (or even no) isopentane from the olefin feed.

BACKGROUND

It is desired to have a process to increase gasoline production by consuming low value isobutane and pentenes and producing a high quality alkylate gasoline. Others have tried alkylating isobutane with pentenes to improve gasoline production and reduce evaporative hydrocarbon emissions, but the processes using either hydrofluoric or sulfuric acid alkylation catalysts have had significant shortcomings. Hydrofluoric (HF) and sulfuric acid ($H_2SO_4$) alkylation catalysts produce significant amounts of isopentane and/or n-pentane during the alkylation of pentenes, and both isopentane and n-pentane have undesirably high Reid Vapor Pressures.

Alkylate gasoline is a highly desirable blending component for motor gasoline with its high octane, low sulfur level and no aromatics. As the gasoline specifications have become tightened worldwide due to heightened environmental concerns, the demand for increased use of alkylate gasoline has been increasing steadily over the years. Most of the refineries in United States already have isoparaffin alkylation units that alkylate isobutane with $C_3$ and $C_4$ olefins from fluid catalytic cracker (FCC) units to produce alkylate gasoline. The FCC units also produce a light gasoline fraction, containing substantial amount of $C_5$-$C_6$ olefins, and due to the difficulties in performing alkylations with them, they are currently blended into the gasoline pool.

Alkylation of $C_5$ olefins has been practiced to only a limited extent in the industry so far. There is a trend suggesting that it would be desired to have more of the $C_5$ olefins be alkylated in the future to help meet tighter environmental regulations. There remains a substantial need to develop an efficient alkylation process for $C_5$ olefins.

Conventional alkylation processes using HF catalyst are not effective in alkylating $C_5$ olefins. During the pentenes alkylation with isobutane, the HF alkylation process generates substantial amounts of isopentane through a hydrogen transfer reaction. This is highly undesirable due to the high Reid Vapor Pressure (RVP) of isopentane (21 RVP for isopentane vs. 6-7 maximum RVP specification for gasoline). An example of the high RVP issue with the HF alkylation process is shown in U.S. Pat. No. 5,382,744 by Abbott el al., which showed that alkylation of 2-methly-2-butene converts about 70 mol % of the pentene to isopentane via hydrogen transfer. In the patent, Abbott et al. found that recycling of isopentane to the reactor reduces the isopentane formation somewhat. However, the recycling of isopentane would make the overall process complicated and raise the cost.

Conventional alkylation processes using $H_2SO_4$ catalysts are less susceptible to the hydrogen transfer than processes using HF catalyst, but still from about 0% up to 20% of C5 olefins are converted to isopentane during the alkylation process using $H_2SO_4$ catalyst (Stratco report, published in 1999 by Randall Peterson, David Graves, Ken Kranz and David Buckler). The $H_2SO_4$ alkylation process for alkylating $C_5$ olefins also increases the acid consumption. The $H_2SO_4$ alkylation processes are highly susceptible to cyclopentene and diene contaminants. The cyclopentene, dienes and other contaminants further increase the acid consumption to an even higher level. To control the acid consumption, a very low reaction temperature of less than 10° C. may need to be used for the processes using $H_2SO_4$ catalyst, which requires additional equipment and higher cost.

SUMMARY

This application provides a process to make an alkylate gasoline, comprising:

a. providing an olefin feed, comprising at least 8 wt % pentenes, a butene, and less than 60 wt % isopentane;

b. providing an isoparaffin feed comprising an isobutane; and c. alkylating the olefin feed with the isoparaffin feed using an acidic ionic liquid alkylation catalyst under alkylation conditions to make the alkylate gasoline;

wherein a yield of the isopentane in the alkylate gasoline corresponds to less than 15 mol % of C5 olefins in the olefin feed and wherein the alkylate gasoline has a final boiling point from 370° F. (187.8 degree Celsius) to 400° F. (204.4 degree Celsius) and a RON of 85 or greater.

This application also provides an alkylation process comprising:

alkylating an olefin feed with an isoparaffin feed comprising an isobutane using an acidic ionic liquid alkylation catalyst under alkylation conditions to produce an alkylate gasoline, wherein the olefin feed comprises at least 8 wt % pentenes and less than 60 wt % isopentane;

wherein a yield of the isopentane in the alkylate gasoline corresponds to less than 15 mol % of C5 olefins in the olefin feed, wherein the alkylate gasoline has a final boiling point from 370° F. (187.8 degree Celsius) to 400° F. (204.4 degree Celsius) and a RON of 85 or higher; and wherein an n-pentane product yield relative to a total olefin content in the olefin feed is from zero to less than 0.2 mol/mol.

Additionally, this application provides an alkylate gasoline, comprising less than 0.1 wt % olefins, less than 0.1 wt % aromatics, less than 1.8 wt % $C_{12+}$ hydrocarbons, and greater than 60 wt % $C_8$ hydrocarbons and $C_9$ hydrocarbons, wherein an amount of a trimethylpentane in the $C_8$ hydrocarbons is from 70 to 80 wt % and a second amount of a trimethylhexane in the $C_9$ hydrocarbons is from 80 to 90 wt %.

The present invention may suitably comprise, consist of, or consist essentially of, the elements in the claims, as described herein.

GLOSSARY

"Olefin" refers to a class of unsaturated aliphatic hydrocarbons having one or more double bonds "Pentenes" are alkenes with the chemical formula $C_5H_{10}$. Each pentene molecule contains one double bond within its molecular structure. There are a total of six different pentene compounds, differing from each other by whether the carbon atoms are attached linearly or in a branched structure, and whether the double bond has a cis- or trans-form.

"Isoparaffin" refers to a branched isomer of a straight-chain paraffin molecule.

"Alkylate gasoline" refers to hydrocarbons that are composed of a mixture of high-octane, branched-chain paraffinic hydrocarbons (e.g., isoheptane and isooctane). Alkylate gasoline is a premium gasoline blending stock because it has exceptional antiknock properties and is clean burning.

"Fluid catalytic cracker" (FCC) is a unit that performs a conversion process employed in petroleum refineries to convert the high-boiling, high-molecular weight hydrocarbon fractions of petroleum crude oils to more valuable FCC gasoline, olefinic gases, and other hydrocarbon products.

"Essentially" refers to from 90 wt % to 100 wt % in the context of this disclosure.

"Periodic Table" refers to the version of the IUPAC Periodic Table of the Elements dated Jun. 22, 2007, and the numbering scheme for the Periodic Table Groups is as described in Chemical And Engineering News, 63(5), 27 (1985).

"Acidic ionic liquid" refers to materials consisting entirely of ions, that can donate a proton or accept an electron pair in reactions, and that are liquid below 100° C.

DETAILED DESCRIPTION

We have discovered that an acidic ionic liquid alkylation catalyst is effective in alkylating a $C_5$ olefin feed with isobutane to make excellent quality alkylate gasoline. Our processes can operate in a wide range of feed variation with both excellent operability and product selectivity. For alkylation of a mixed $C_4$ and $C_5$ olefin feed with isobutane, our process with an acidic ionic liquid alkylation catalyst can selectively convert the $C_5$ olefins to alkylate gasoline with a minor (or no) incremental production of isopentane. In one embodiment, for olefin feeds comprising high $C_5$ olefin and isopentane, our processes are able to convert both isopentane and $C_5$ olefins in the feed to alkylate gasoline and thus, effectively lower the isopentane content in the alkylate gasoline product.

Alkylation of $C_5$ olefins (pentenes or amylenes) with isoparaffins comprising isobutane would provide many benefits to a refinery. A refinery would be able to increase the alkylate gasoline production volume by alkylating the $C_5$ olefins with isobutane and the alkylate gasoline has a significantly higher value than the isobutane and the mixed pentene starting materials.

In one embodiment, by converting the high RVP (Reid Vapor Pressure) and olefinic pentenes from a Fluid Catalytic Cracker (FCC) gasoline to generate low RVP alkylate gasoline by the processes of our invention, the overall gasoline pool RVP and olefin content are significantly reduced. The production of additional clean, low RVP alkylate gasoline gives the refinery more flexibility in gasoline blending.

The olefin feed that is useful in the processes herein comprise at least 8 wt % of pentenes and less than 60 wt % isopentane. In one embodiment, the olefin feed comprises greater than 20 wt % of pentenes. In one embodiment, the olefin feed comprises from at least 8 wt % to 100 wt % pentenes. The amount of the pentenes in the olefin feed can range broadly, for example the amount of the pentenes in the olefin feed can be from 10 to 100 mol %, from 10 to 99.9 mol %, or 35 to 100 mol % of a total olefins in the olefin feed.

In one embodiment, the olefin feed additionally comprises a butene, such as from 1 to 80 wt % butene. In one embodiment, the olefin feed comprises $C_3$, $C_4$, and $C_5$ olefins.

The olefin feed can come from any source, not just from a refinery. Examples of suitable olefin feeds include hydrocarbons comprising pentenes which could come, for example, from FCC, from a coker unit, naphtha cracking, gas-to-liquid (GTL) processes, or derived via dehydrogenation of pentane, such as from natural gas liquid dehydrogenation or bio-material dehydrogenation. The feeds may come directly from different sources, or can be blended. In one embodiment the olefin feed is from a FCC unit in a refinery. The processes may additionally comprise isolating a $C_5$ olefin stream from a FCC unit to provide the olefin feed and the alkylating converts the $C_5$ olefin stream to the alkylate gasoline without needing to increase a throughput from the FCC unit.

In one embodiment, the olefin feed comprises 1-pentene, such as from greater than 2 wt % to 10 wt % 1-pentene.

The olefin feed may comprise varying levels of n-pentane. In one embodiment, the olefin feed comprises from zero to 10 wt % n-pentane, such as 4 wt % or less, or from 0.1 wt % to 8 wt % n-pentane.

In one embodiment, the olefin feed comprises greater than 5 wt % isopentane, such as from greater than 12.7 wt % to 55 wt % of the isopentane. In one embodiment, the olefin feed comprises greater than 12.7 wt % of the isopentane and the alkylating lowers a content of the isopentane in the alkylate gasoline.

In one embodiment, the processes may comprise selectively hydrogenating a refinery olefin stream to make the olefin feed. The selectively hydrogenating can reduce the dienes in the olefin feed. For example, after the selective hydrogenation the olefin feed can comprise less than 1 wt % dienes, or from zero to 0.5 wt % dienes. Reducing the level of dienes and cyclopentene in the olefin feed can reduce the rate of conjunct polymer formation during the alkylating and/or improve the alkylate gasoline product quality, e.g., by reducing formation of gum or heavy hydrocarbons with high boiling point. Depending on the severity of the selective hydrogenation (e.g., temperature, hydrogen flow, hydrogen partial pressure, residence time, and choice of the hydrogenation catalyst), different extents of diene removal and isomerization of the olefins in the olefin feed will occur. In one embodiment, the conditions for selectively hydrogenating are selected to be mild, and the mild conditions remove only a portion of the dienes. In one embodiment, the conditions for selectively hydrogenating are chosen to also perform olefin isomerization, and the olefin isomerization can be limited to shifting of double bonds in molecules in the olefin feed, such as converting 1-pentene to 2-pentene or converting methyl-1-butenes to methyl-2-butenes. Conversion of 1-pentene to 2-pentene, thereby increasing the relative amount of 2-pentene in the olefin feed, can increase the RON and MON of the alkylate gasoline produced via alkylation with an ionic liquid catalyst.

In one embodiment, the processes may additionally comprise hydroisomerizing a refinery olefin stream to make an olefin feed that has a reduced amount of 1-butene and an increased amount of 2-butene. Increasing the amount of 2-butene in the olefin feed can increase the RON and/or a MON of the alkylate gasoline.

In one embodiment, the processes may comprise selectively hydrogenating the olefin feed to increase the RON and/or a MON of the alkylate gasoline by at least about 0.5. In a sub-embodiment, the RON is increased by 0.5 to 4.0.

In one embodiment, the alkylating can convert essentially all of the olefins in the olefin feed. In one embodiment, the alkylating converts greater than 98 wt %, or even 100 wt %, of the olefins in the olefin feed.

Alkylate Gasoline

In one embodiment, the alkylate gasoline made by the processes disclosed herein has one or more of a high Research Octane Number (RON), a high Motor Octane Number (MON), a low final boiling point, and low Reid Vapor Pressure (RVP). The alkylate gasoline produced by the processes of this invention can have one or more desired properties, including a low final boiling point, a high RON, high MON, low RVP, low aromatics, low olefins, and low sulfur. In one or more embodiments, the alkylate gasoline has a final boiling point from 370° F. (187.8 degree Celsius) to 400° F. (204.4 degree Celsius).

Research Octane Number (RON) is determined using ASTM D2699-15 (REV A), Standard Test Method for Research Octane Number of Spark-Ignition Engine Fuel. Additionally, the RON (GC) can be calculated from gas chromatography boiling range distribution data. The RON (GC) calculation is described in the publication, Anderson, P. C., Sharkey, J. M., and Walsh, R. P., "Journal Institute of Petroleum", 58 (560), 83 (1972). Another measure of the octane number of a fuel is the Motor Octane Number (MON). MON correlates with commercial automotive spark-ignition engine antiknock performance under severe conditions of operation. MON can be determined by ASTM D2700-16.

In one or more embodiments, the alkylate gasoline has a high RON, such as 85 or higher, from 90.0 or higher, from 85.0 to 96.0, or from 90.0 to 94.5.

The alkylate gasoline contains from zero to less than 0.1 wt % aromatics, from zero to less than 0.1 wt % olefins, and can also have low sulfur.

In one embodiment, the alkylate gasoline has an amount of a trimethylpentane in C8 hydrocarbons in the alkylate gasoline that is greater than 50 wt %, such as from 70 to 95 wt %.

In one embodiment, the alkylate gasoline has an amount of trimethylhexane in C9 hydrocarbons in the alkylate gasoline that is greater than 70 wt %, such as from 85 to 95 wt %.

In some embodiments, the alkylate gasoline comprises a C5+alkylate fraction having a RVP less than 7 psi, such as from 2.3 to 6.0 psi, or from 2.0 to 5.5 psi. In one embodiment the RVP is less than 4.0 psi. RVP can be determined by ASTM D323-15a, "Standard Test Method for Vapor Pressure of Petroleum Products (Reid Method)".

In some embodiments, the alkylate gasoline has a $C_{5+}$ average density greater than 0.65 g/cc, such as from 0.68 to 0.74 g/cc.

In one embodiment, the alkylate gasoline comprises from zero to less than 0.1 wt % olefins, from zero to less than 0.1 wt % aromatics, from zero to less than 1.8 wt % $C_{12+}$ hydrocarbons, and greater than 60 wt % combined $C_8$ and $C_9$ hydrocarbons. In a sub-embodiment, this alkylate gasoline can comprise a high level of trimethylalkanes, which impart a high RON to the alkylate gasoline. For example, the alkylate gasoline can comprise an amount of a trimethylpentane in the $C_8$ hydrocarbons greater than 50 wt %, such as from 70 to 95 wt %, and a second amount of a trimethylhexane in the $C_9$ hydrocarbons greater than 70 wt %, such as from 85 to 95 wt %. In a sub-embodiment, the alkylate gasoline comprises from 0.1 to less than 1 wt % $C_{12+}$ hydrocarbons.

In one embodiment the alkylate gasoline comprises greater than 60 wt % $C_8$ hydrocarbons and $C_9$ hydrocarbons, such as from 61 to 90 wt % or 65 to 80 wt %. In one embodiment, the alkylate gasoline comprises greater than 10 wt % $C_9$ hydrocarbons, such as from 13 to 42 wt %. In one embodiment, the alkylate gasoline comprises greater than 20 wt % $C_8$ hydrocarbons, such as from 25 to 65 wt % $C_8$ hydrocarbons.

In one embodiment a $C_5$ olefin stream from a FCC unit can be easily isolated and then this $C_5$ olefin stream provides an attractive alternative source of olefins that can be converted to additional amounts of high quality, clean, alkylate gasoline without increasing the FCC unit throughput.

In one embodiment, the process is an effective alkylation process for a mixed $C_4/C_5$ olefin feed with isobutane using an acidic ionic liquid alkylation catalyst where the process selectively converts $C_5$ olefins to alkylate gasoline with a minor incremental production of isopentane.

In one embodiment, with high $C_5$ olefin content (e.g., from greater than 8 wt % to 40 wt % total pentenes) and high isopentane content (e.g., from greater than 12.7 wt % to 55 wt %) in the olefin feed, our process is able to convert both isopentane and $C_5$ olefins in the olefin feed to alkylate gasoline and also effectively lower the isopentane content in the alkylate gasoline product.

Alkylating

The processes comprise alkylating the olefin feed with the isoparaffin feed using an acidic ionic liquid alkylation catalyst under alkylation conditions. For example, the alkylating can be done at an alkylation temperature greater than −20° C., such as from −15° C. to 100° C., or from −10° C. to 50° C. In one embodiment, the alkylation conditions may include one or more of a catalyst volume in an alkylation reactor of 2 vol % to 50 vol %, an alkylation temperature of −10° C. to 100° C., an alkylating pressure of 300 kPa to 2500 kPa, an isoparaffin to olefin molar ratio of 2 to 16 and a residence time of 30 seconds to 1 hour.

While we do not want to be bound by the theory, data in hand suggests that the acidic ionic liquid alkylation catalyst does not have a high H-transfer tendency, unlike the conventional HF alkylation catalyst and to a lesser extent than the $H_2SO_4$ alkylation catalyst. The acidic ionic liquid alkylation catalyst can preferably make the primary alkylation product of isobutane with $C_5$ olefins that is predominately trimethylhexane. With high reactivity in an alkylation reactor, the acidic ionic liquid alkylation catalyst is uniquely able to convert isopentane in the olefin feed when the isopentane concentration is above a threshold value, somewhere between 12.7 to 29.8 wt % isopentane in the olefin feed or 1-3 wt % isopentane in the combined feed (isobutane and olefin feed).

In one embodiment, the acidic ionic liquid alkylation catalyst conducts simultaneous conversion of the isobutane and the isopentane into the alkylate gasoline during the alkylating. In one embodiment, the acidic ionic liquid alkylation catalyst conducts simultaneous conversion of isobutane and isopentane into high quality alkylate gasoline products. The simultaneous conversion of isobutane and isopentane appears to be unique, and this may allow co-processing of isopentane and isobutane in the alkylation reactor, which was not possible with earlier conventional alkylation catalysts.

Acidic Ionic Liquid

Examples of acidic ionic liquid alkylation catalysts and their use for alkylation of paraffins with olefins are taught, for example, in U.S. Pat. Nos. 7,432,408 and 7,432,409, 7,285,698, and U.S. patent application Ser. No. 12/184,069, filed Jul. 31, 2008. In one embodiment, the acidic ionic liquid alkylation catalyst is a composite ionic liquid alkylation catalyst, wherein the cations come from a hydrohalide of an alkyl-containing amine or pyridine, and the anions are composite coordinate anions coming from two or more metal compounds.

The most common acidic ionic liquids are those prepared from organic-based cations and inorganic or organic anions. The acidic ionic liquid alkylation catalyst is composed of at least two components which form a complex. The acidic ionic liquid alkylation catalyst comprises a first component and a second component. The first component of the acidic ionic liquid alkylation catalyst will typically comprise a Lewis acid compound selected from components such as Lewis acid compounds of Group 13 metals, including aluminum halides, alkyl aluminum dihalides, gallium halide, and alkyl gallium halide (see the Periodic Table, which defines the elements that are Group 13 metals). Other Lewis acid compounds besides those of Group 13 metals may also be used. In one embodiment the first component is aluminum halide or alkyl aluminum dihalide. For example, aluminum trichloride ($AlCl_3$) may be used as the first component for preparing the ionic liquid alkylation catalyst. In one embodiment, the alkyl aluminum dihalides that can be used can have the general formula $Al_2X_4R_2$, where each X represents a halogen, selected for example from chlorine and bromine, each R represents a hydrocarbyl group comprising 1 to 12 atoms of carbon, aromatic or aliphatic, with a branched or a linear chain. Examples of alkyl aluminum dihalides include dichloromethylaluminum, dibromomethylaluminum, dichloroethylaluminum, dibromoethylaluminum, dichloro n-hexylaluminum, dichloroisobutylaluminum, either used separately or combined.

The second component making up the acidic ionic liquid can be an organic salt or mixture of salts. These salts may be characterized by the general formula Q+A−, wherein Q+ is an ammonium, phosphonium, boronium, oxonium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $Al_2Cl_7^-$, $Al_3Cl_{10}^-$, $GaCl_4^-$, $Ga_2Cl_7^-$, $Ga_3Cl_{10}^-$, $ASF_6^-$, $TaF_6^-$, $CuCl_2^-$, $FeCl_3^-$, $AlBr_4^-$, $Al_2Br_7^-$, $Al_3Br_{10}^-$, $SO_3CF_3^-$, and 3-sulfurtrioxyphenyl.

In one embodiment the second component is selected from those having quaternary ammonium halides containing one or more alkyl moieties having from about 1 to about 9 carbon atoms, such as, for example, trimethylammonium hydrochloride, methyltributylammonium, 1-butyl pyridinium, or alkyl substituted imidazolium halides, such as for example, 1-ethyl-3-methyl-imidazolium chloride.

In one embodiment, the acidic ionic liquid comprises a monovalent cation selected from the group consisting of a pyridinium ion, an imidazolium ion, a pyridazinium ion, a pyrazolium ion, an imidazolinium ion, a imidazolidinium ion, an ammonium ion, a phosphonium ion, and mixtures thereof. Examples of possible cations (Q+) include a butylethylimidazolium cation [beim], a butylmethylimidazolium cation [bmim], butyldimethylimidazolium cation [bmmim], decaethylimidazolium cation [dceim], a decamethylimidazolium cation [dcmim], a diethylimidazolium cation [eeim], dimethylimidazolium cation [mmim], an ethyl-2,4-dimethylimidazolium cation [e-2,4-mmim], an ethyldimethylimidazolium cation [emmim], an ethylimidazolium cation [eim], an ethylmethylimidazolium [emim] cation, an ethylpropylimidazolium cation [epim], an ethoxyethylmethylimidazolium cation [etO-emim], an ethoxydimethylimidazolium cation [etO-mmim], a hexadecylmethylimidazolium cation [hexadmim], a heptylmethylimidazolium cation [hp-mim], a hexaethylimidazolium cation [hxeim], a hexamethylimidazolium cation [hxmim], a hexadimethylimidazolium cation [hxmmim], a methoxyethylmethylimidazolium cation [meO-emim], a methoxypropylmethylimidazolium cation [meO-prmim], a methylimidazolium cation [mim], dimethylimidazolium cation [mmim], a methylnonylimidazolium cation [mnim], a methylpropylimidazolium cation [mpim], an octadecylmethylimidazolium cation [octadmim], a hydroxylethylmethylimidazolium cation [OH-emim], a hydroxyloctylmethylimidazolium cation [OH-omim], a hydroxylpropylmethylimidazolium cation [OH-prmim], an octylmethylimidazolium cation [omim], an octyldimethylimidazolium cation [ommim], a phenylethylmethylimidazolium cation [ph-emim], a phenylmethylimidazolium cation [ph-mim], a phenyldimethylimidazolium cation [ph-mmim], a pentylmethylimidazolium cation [pnmim], a propylmethylimidazolium cation [prmim], a 1-butyl-2-methylpyridinium cation[1-b-2-mpy], 1-butyl-3-methylpyridinium cation[1-b-3-mpy], a butylmethylpyridinium [bmpy] cation, a 1-butyl-4-dimethylacetylpyridinium cation [1-b-4-DMApy], a 1-butyl-4-35 methylpyridinium cation[1-b-4-mpy], a 1-ethyl-2-methylpyridinium cation[1-e-2-mpy], a 1-ethyl-3-methylpyridinium cation[1-e-3-mpy], a 1-ethyl-4-dimethylacetylpyridinium cation[1-e-4-DMApy], a 1-ethyl-4-methylpyridinium cation[1-e-4-mpy], a 1-hexyl-5 4dimethylacetylpyridinium cation[1-hx-4-DMApy], a 1-hexyl-4-methylpyridinium cation[1-hx-4-mpy], a 1-octyl-3-methylpyridinium cation[1-o-3-mpy], a 1-octyl-4-methylpyridinium cation[1-o-4-mpy], a 1-propyl-3-methylpyridinium cation[1-pr-3-mpy], a 1-propyl-4-methylpyridinium cation[1-pr-4-mpy], a butylpyridinium cation [bpy], an ethylpyridinium cation [epy], a heptylpyridinium cation [hppy], a hexylpyridinium cation [hxpy], a hydroxypropylpyridinium cation [OH-prpy], an octylpyridinium cation [opy], a pentylpyridinium cation [pnpy], a propylpyridinium cation [prpy], a butylmethylpyrrolidinium cation [bmpyr], a butylpyrrolidinium cation [bpyr], a hexylmethylpyrrolidinium cation [hxmpyr], a hexylpyrrolidinium cation [hxpyr], an octylmethylpyrrolidinium cation [ompyr], an octylpyrrolidinium cation [opyr], a propylmethylpyrrolidinium cation [prmpyr], a butylammonium cation [b-N], a tributylammonium cation [bbb-N], a tetrabutylammonium cation [bbbb-N], a butylethyldimethylammonium cation [bemm-N], a butyltrimethylammonium cation [bmmm-N], a N,N,N-trimethylethanolammonium cation [choline], an ethylammonium cation [e-N], a diethylammonium cation [ee-N], a tetraethylammonium cation [eeee-N], a tetraheptylammonium cation [hphphphp-N], a tetrahexylammonium cation [hxhxhxhx-N], a methylammonium cation [m-N], a dimethylammonium cation [mm-N], a tetramethylammonium cation [mmmm-N], an ammonium cation [N], a butyldimethylethanolammonium cation [OHe-bmm-N], a dimethylethanolammonium cation [OHe-mm-N], an ethanolammonium cation [OHe-N], an ethyldimethylethanolammonium cation [OHe-emm-N], a tetrapentylammonium cation [pnpnpnpn-N], a tetrapropylammonium cation [prprprpr-N], a tetrabutylphosphonium cation [bbbb-P], a tributyloctylphosphonium cation [bbbo-P], or combinations thereof.

In one embodiment, the second component is selected from those having quaternary phosphonium halides containing one or more alkyl moieties having from 1 to 12 carbon atoms, such as, for example, trialkyphosphonium hydrochloride, tetraalkylphosphonium chlorides, and methyltrialkyphosphonium halide.

In one embodiment, the acidic ionic liquid comprises an unsubstituted or partly alkylated ammonium ion.

In one embodiment, the acidic ionic liquid is chloroaluminate or a bromoaluminate. In one embodiment the acidic ionic liquid is a quaternary ammonium chloroaluminate ionic liquid having the general formula RR' R" N $H^+Al_2Cl_7^-$, wherein R, R', and R" are alkyl groups containing 1 to 12 carbons. Examples of quaternary ammonium chloroaluminate ionic liquids are an N-alkyl-pyridinium chloroaluminate, an N-alkyl-alkylpyridinium chloroaluminate, a pyridinium hydrogen chloroaluminate, an alkyl pyridinium hydrogen chloroaluminate, a di alkyl-imidazolium chloroaluminate, a tetra-alkyl-ammonium chloroaluminate, a tri-alkyl-ammonium hydrogen chloroaluminate, or a mixture thereof.

The presence of the first component should give the acidic ionic liquid a Lewis or Franklin acidic character. Generally, the greater the mole ratio of the first component to the second component, the greater is the acidity of the acidic ionic liquid.

For example, a typical reaction mixture to prepare n-butyl pyridinium chloroaluminate ionic liquid is shown below:

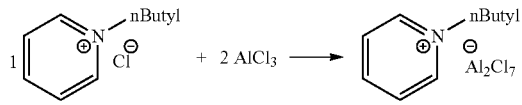

In one embodiment, the acidic ionic liquid utilizes a co-catalyst to provide enhanced or improved alkylation activity. Examples of co-catalysts include alkyl halide or hydrogen halide. A co-catalyst can comprise, for example, anhydrous HCl or organic chloride (see, e.g., U.S. Pat. No. 7,495,144 to Elomari, and U.S. Pat. No. 7,531,707 to Harris et al.). When organic chloride is used as the co-catalyst with the acidic ionic liquid, HCl may be formed in situ in the apparatus either during the alkylating or during post-processing of the output of the alkylating. In one embodiment, the alkylating with the acidic ionic liquid is conducted in the presence of a hydrogen halide, e.g., HCl.

In one embodiment, the acidic ionic liquid alkylation catalyst additionally comprises a Brønsted acid. In one embodiment, the acidic ionic liquid alkylation catalyst comprises an ionic liquid catalyst and a Brønsted acid. In these embodiments, the Brønsted acid acts as a promoter or co-catalyst. Examples of Brønsted acids are sulfuric acid, HCl, HBr, HF, phosphoric acid, HI, etc. Other strong acids that are proton donors can also be suitable Brønsted acids. In one embodiment, the Brønsted acid is produced internally within the process by the conversion of an alkyl halide into the corresponding hydrogen halide. In one embodiment the Brønsted acid is formed by a reaction of a Lewis acid component of an ionic liquid, such as chloroaluminate ions for instance reacting with a weakly acidic proton donor such as an alcohol or water to form HCl.

The alkyl halides that may be used include alkyl bromides, alkyl chlorides and alkyl iodides. Such alkyl halides include but are not limited to isopentyl halides, isobutyl halides, t-butyl halides, n-butyl halides, propyl halides, and ethyl halides. Alkyl chloride versions of these alkyl halides can be preferable when chloroaluminate ionic liquids are used. Other alkyl chlorides or alkyl halides having from 1 to 8 carbon atoms can be also used. The alkyl halides may be used alone or in combination.

When used, the alkyl halide or hydrogen halide co-catalysts are used in catalytic amounts. In one embodiment, the amounts of the alkyl halides or hydrogen halide should be kept at low concentrations and not exceed the molar concentration of the $AlCl_3$ in the acidic ionic liquid. For example, the amounts of the alkyl halides or hydrogen halide used may range from 0.05 mol %-100 mol %, or 0.05 mol %-10 mol %, of the Lewis acid $AlCl_3$ in the acidic ionic liquid in order to keep the acidity of the acidic ionic liquid alkylation catalyst at the desired performing capacity.

In one embodiment, the acidic ionic liquid alkylation catalyst comprises an ionic liquid catalyst and a Brønsted acid. In this embodiment, the Brønsted acid acts as a promoter or co-catalyst. Examples of Brønsted acids are sulfuric acid, HCl, HBr, HF, phosphoric acid, HI, etc. Other strong acids that are proton donors can also be suitable Brønsted acids. In one embodiment, the Brønsted acid is produced internally within the process by the conversion of an alkyl halide into the corresponding hydrogen halide.

In one embodiment, the process can additionally comprise recycling an excess of the isoparaffin feed to the alkylating. For example, the process can include distilling out an excess isoparaffin after the alkylating and then recycling the excess isoparaffin to the alkylating.

EXAMPLES

Example 1

Ionic Liquid Alkylation Catalyst

Various acidic ionic liquid alkylation catalysts made of metal halides, such as $AlCl_3$, $AlBr_3$, $GaCl_3$, $GaBr_3$, $InCl_3$, and $InBr_3$ could be used for catalytic processes. N-butylpyridinium chloroaluminate ($C_5H_5NC_4H_9Al_2Cl_7$) was the acidic ionic liquid alkylation catalyst used in the following examples. This acidic ionic liquid alkylation catalyst had a density of 1.34 g/cc and had the composition shown in Table 1.

TABLE 1

| Composition of Fresh Acidic Ionic Liquid Alkylation Catalyst Fresh Ionic Liquid Alkylation Catalyst | |
|---|---|
| Al, wt % | 11.18 |
| Cl, wt % | 56.5 |
| C, wt % | 25.95 |
| H, wt % | 3.29 |
| N, wt % | 3.32 |

Example 2

Feed Compositions

The isobutane feeds used in this example were either refinery isobutane feed consisting of 85 wt % isobutane and 15 wt % n-butane, or 100 wt % pure chemical grade isobutane. The isobutane streams were thoroughly dried to less than 1 wppm water by passing the isobutane feeds through a fixed bed containing a molecular sieve adsorbent.

Five different olefin feeds used in this example were refinery olefin streams from a Fluid Catalytic Cracker (FCC) containing varying amounts of $C_5$ olefins. The olefin feeds all had 1 wt % or less of $C_3$ olefins, and no ethylene. These olefin feeds were also thoroughly dried to less than 1 wppm water by passing the olefin feeds through a fixed bed containing a molecular sieve adsorbent. The water contents in the dried isobutane and olefin feeds were measured using a GE Panametrics on-line moisture analyzer with an aluminum oxide moisture sensor probe.

The detailed compositions of the five different olefin feeds are summarized in Table 2.

TABLE 2

| Composition of Olefin Feeds | | | | | |
|---|---|---|---|---|---|
| Mol % of C5 Olefins/Total C3-C5 Olefins | 2.2 | 14.2 | 39.5 | 59.3 | 75.0 |
| Olefin Feed | Feed #1 | Feed #2 | Feed #3 | Feed #4 | Feed #5 |
| Composition, wt % | | | | | |
| Propane | 2.7 | 1.6 | 0.8 | 0.5 | 0.01 |
| Propylene | 1.1 | 0.8 | 0.9 | 0.6 | 0.01 |
| Isobutane | 30.6 | 30.5 | 17.5 | 9.3 | 0.5 |
| n-Butane | 9.8 | 4.7 | 3.0 | 2.0 | 1.5 |
| Butenes (sum of C4= isomers) | 51.0 | 40.3 | 24.9 | 16.1 | 9.7 |
| Isopentane | 3.2 | 12.7 | 29.8 | 37.8 | 48.5 |
| n-Pentane | 0.1 | 0.7 | 2.1 | 3.1 | 3.7 |
| 3-Methyl-1-Butene | | 0.6 | 1.4 | 1.6 | 2.2 |
| 1-Pentene | | 1.8 | 4.5 | 6.7 | 7.9 |
| 2-Methyl-1-Butene | 1.5 (total C5=) | 2.2 | 6.8 | 11.3 | 10.3 |
| 2-Pentenes | | 3.1 | 6.4 | 7.9 | 11.9 |
| 2-Methyl-2-Butene | | 0.9 | 2.2 | 3.3 | 3.8 |
| Cyclopentene | 0 | | 0.15 | | |
| 1-3-Butadiene | 0 | 0.07 | 0.03 | 0.03 | ~0.03 |
| Isoprene (2-Methyl-1,3-Butadiene) | 0 | | 0.11 | | |
| t-1,3-Pentadiene | 0 | | 0.04 | | |
| Cyclopentadiene | 0 | | 0.05 | | |
| Sum of C5= isomers, wt % | 1.5 | 8.6 | 21.4 | 30.7 | 36.2 |
| Sum of C4 & C5 dienes, wt % | <0.01 | | 0.23 | | |
| Total olefin content, wt % | 53.6 | 49.7 | 47.0 | 47.4 | 45.9 |
| mol % C3= in total olefins (C3=, C4= & C5=) | 2.7 | 2.2 | 2.8 | 1.8 | 0.0 |
| mol % C4= in total olefins (C3=, C4= & C5=) | 95.0 | 83.6 | 57.6 | 38.9 | 25.0 |
| mol % C5= in total olefins (C3=, C4= & C5=) | 2.2 | 14.2 | 39.7 | 59.3 | 75.0 |
| Sum | 100.0 | 100.0 | 100.0 | 100.0 | 100.0 |

Note:
Feed #3 was analyzed for precise cyclopentene and diene content measurements. Feed #2, Feed #4 and Feed #5 are expected to have similar amounts of cyclopentene and dienes.

Feed #1 was a typical refinery feed for a $C_4$ olefin alkylation plant and is a comparative example. The $C_5$ olefin content was low, 1.5 wt %, and the amount of $C_5$ olefin relative to the total olefins was only 2.2 mol %. The feed #1 contained only 3.2 wt % isopentane.

For this $C_5$ olefin alkylation study, olefin feeds with higher amounts of $C_5$ olefins were studied (Feed #2 through Feed #5). The $C_5$ olefin content relative to the total olefins ($C_3$, $C_4$ and $C_5$ olefins) in the olefin feeds varied in these samples from 14.2 mol % to 75 mol %. These olefin feeds contained from 12.7 to 48.5 wt % isopentane. These olefin feeds contained from 0.7 to 3.7 wt % n-pentane.

The olefin Feeds #2 through #5 were selectively hydrogenated at mild conditions to reduce their diene contents. These olefin feeds still contained about 300-700 ppm of butadiene, 1100 ppm of isoprene (2-methyl-1,3-butadiene), 400 ppm of trans-1,3-pentadiene and 500 ppm of cyclopentadiene. The selective hydrogenation of Feed #1, the comparative base case, was more extensive, and nearly complete removal of butadiene was observed (less than the detection limit of 100 ppm by GC).

Examples 3 through 7

Alkylation Conditions and Alkylate Gasoline Products

Evaluation of $C_4$/$C_5$ olefins alkylation with isobutane was performed in a continuously stirred tank reactor with the feeds described previously. A 10:1 molar mixture of isobutane and olefin was fed to the reactor while vigorously stirring. An acidic ionic liquid alkylation catalyst as described in Example 1 was fed to the reactor via a second inlet port targeted to occupy about 3-5 vol % in the reactor. A small amount of n-butyl chloride was added to produce anhydrous HCl gas in situ. In these examples, the acidic ionic liquid alkylation catalyst is a N-butylpyridinium-heptachlorodialuminate and the Brønsted acid is hydrogen chloride. The average residence time in the reactor (combined volume of feeds and catalyst) was about 5 minutes. The outlet pressure was maintained at 150 psig (1034 kPa) and the reactor temperature was maintained at 95° F. (35° C.) using a cooling coil.

The reactor effluent was separated with a coalescing separator into a hydrocarbon phase and an ionic liquid alkylation catalyst phase. The hydrocarbon phase was further separated with three distillation columns into multiple streams, including: a gas stream containing a $C_3^-$ fraction, an $nC_4$ stream, an $iC_4$ stream, and an alkylate gasoline stream. To maintain the activity of the acidic ionic liquid alkylation catalyst, the separated ionic liquid alkylation catalyst was sent to a regeneration reactor for reduction of the conjunct polymer level in the acidic ionic liquid alkylation catalyst. The conjunct polymer level in the acidic ionic liquid alkylation catalyst was maintained at 3-6 wt %. The amount of conjunct polymer in the acidic ionic liquid alkylation catalyst was determined using an FT-IR quantitation method described in U.S. Pat. No. 9,290,702B2.

The alkylation conditions and alkylate gasoline product properties from the various feeds are summarized in Table 3.

TABLE 3

Physical Properties of Alkylate Gasoline Products

| | Example 3 Base Case Alkylate Feed #1 | Example 4 Invention Alkylate Feed #2 | Example 5 Invention Alkylate Feed #3 | Example 6 Invention Alkylate Feed #4 | Example 7 Invention Alkylate Feed #5 |
|---|---|---|---|---|---|
| Olefin Feed Source | | | | | |
| Mol % of C5 Olefins/Total Olefins | 2.2 | 14.2 | 39.5 | 59.3 | 75.0 |
| Reactor Temperature, ° F. | 95 | 95 | 95 | 95 | 95 |
| Reactor Pressure, psig | 150 | 150 | 150 | 150 | 150 |
| Isobutane/Olefin Molar Ratio | 10 | 10 | 10 | 10 | 10 |
| Conversion of olefins, wt % | 100.0 | 100.0 | 100.0 | 100.0 | 100.0 |
| Alkylate Gasoline Product Properties | | | | | |
| Engine Test RON | 94.5 | 92.9 | 92.8 | 92.6 | 90.0 |
| Engine Test MON | 92.3 | 90.6 | 90.2 | 90.1 | 89.0 |
| Engine Test, (R + M)/2 | 93.4 | 91.8 | 91.5 | 91.4 | 89.5 |
| D86 Distillation (deg F.) | | | | | |
| T10 | 154 | 144 | 137 | 129 | 118 |
| T30 | 212 | 214 | 216 | 214 | 202 |
| T50 | 224 | 229 | 230 | 234 | 241 |
| T70 | 239 | 239 | 246 | 247 | 257 |
| FBP | 379 | 383 | 377 | 381 | 385 |
| C5+ Alkylate RVP | 2.1 | 2.9 | 3.4 | 4.4 | 5.1 |
| C5+ Alkylate Average density, g/cc | 0.71 | 0.71 | 0.71 | 0.70 | 0.70 |
| C5+ Alkylate Composition | | | | | |
| C5 (wt %) | 2.8 | 4.6 | 6.9 | 10.1 | 12.7 |
| C6 (wt %) | 4.6 | 3.2 | 2.8 | 3.8 | 4.3 |
| C7 (wt %) | 7.9 | 5.1 | 4.5 | 5.1 | 3.0 |
| C8 (wt %) | 61.8 | 61.3 | 51.4 | 49.8 | 30.0 |
| C9 (wt %) | 10.4 | 16.1 | 26.2 | 24.7 | 38.8 |
| C10 (wt %) | 5.4 | 3.8 | 3.9 | 3.2 | 6.9 |
| C11 (wt %) | 6.4 | 5.5 | 3.9 | 3.1 | 3.3 |
| C12+ (wt %) | 0.8 | 0.5 | 0.4 | 0.2 | 0.9 |
| Total | 100.0 | 100.0 | 100.0 | 100.0 | 100.0 |
| Trimethylpentane/Total C8 (%) | 83.9% | 72.7% | 76.4% | 70.8% | 71.5% |
| Trimethylhexane/Total C9 (%) | 75.7% | 86.7% | 86.2% | 85.9% | 85.9% |

Research Octane numbers (RONs) and Motor Octane numbers (MONs) were measured by an engine test of the alkylate gasoline products. The distillation boiling point distributions of T10, T30, T50, T70 and the final boiling points were measured using ASTM D86-15, "Standard Test Method for Distillation of Petroleum Products at Atmospheric Pressure". The detailed compositions of the alkylate gasoline products were analyzed using gas chromatography. From the GC compositional data, the Reid Vapor Pressure (RVP) and average density of the $C_{5+}$ alkylate gasolines were calculated.

The base case (Example 3 with Feed #1) showed the typical yield and product properties for alkylation of $C_4$ olefins. Alkylation performance of Example 3 was compared with the other olefin feeds with higher $C_5$ (and varied) olefin feed compositions. Increases of the $C_5$ olefin content in the olefin feed from 14.2 mol % to 75 mol % (Feed #2 through Feed #5), did not affect the unit operation in any negative ways. In all cases, the olefin conversions were maintained at 100% and the residual olefin contents in the alkylate gasoline products were less than 0.1 wt %. These examples demonstrated the process wherein a level of the pentene in the olefin feed was increased and did not create a deleterious formation of a conjunct polymer in the acidic ionic liquid alkylation catalyst during the alkylating. The high $C_5$ olefin containing feeds (Feed #2 through Feed #5) contained a substantial amount of dienes, about 0.23 wt %, and 0.15 wt % cyclopentene. The alkylation process was not affected by the high diene and cyclopentene contents either. The conjunct polymer formation rates were comparable for all the olefin feeds, and the alkylation operations were maintained easily. Unlike the $H_2SO_4$ alkylation process, we did not see any detrimental impact on conjunct polymer formation (i.e., there was no significant increase) with increasing amounts of pentene and dienes in the olefin feeds, which causes an expensive high acid consumption for the $H_2SO_4$ alkylation process.

The alkylate gasoline products had RONs in the range of 94.5 to 90 and MONs in the range of 92.3 to 89. These octane numbers were decreased slightly due to the increased Cys (that came with the feed), a reduction of the $C_8$ hydrocarbons in the alkylate gasoline products, and an increase of the $C_9$ hydrocarbons in the alkylate gasoline products. The $C_9$ hydrocarbon fractions in the alkylate gasoline products were rich in trimethylhexanes (from 75.7 to 85.9 wt %), which have a relatively low RON of 90. The $C_8$ hydrocarbon fractions in the alkylate gasoline products were also rich in trimethylpentanes, which have a high RON of 100.

The final boiling points of the alkylate gasoline products (Examples 3 through 7) were all comparable at 380° F. (193.3 degree Celsius) to 385° F. (196.1 degree Celsius), well below the typical gasoline specification of <430° F. (221.1 degree Celsius), indicating higher quality alkylate gasoline products were produced. It was surprising to find all the alkylate gasoline product examples made with varying $C_5$ olefin contents in the feeds, had the similar, excellent low final boiling points. Consistent with the boiling point distributions, all the alkylate gasoline products had comparable average $C_5^+$ densities, in the range of 0.70-0.71 g/cc. Consistently, the heavy $C_{12}^+$ fractions were less than 1 wt %. These features were far superior to those of any $H_2SO_4$ alkylation processes, where higher final boiling point (over 430° F. [over 221.1° C.]) alkylate gasoline products were commonly obtained with an olefin feed containing substantial amounts of $C_5$ olefins.

Due to the high amount of isopentane that came with the $C_5$ olefin feeds, there was a slight decrease in the T10 distillation points and a slight increase in the RVPs as the amount of isopentane increased from Examples 3 to 7. Still the $C_{5+}$ alkylate gasoline RVP was well below the typical gasoline specification of less than 6-7 psi in all of these examples.

The isopentane and n-pentane that was present in the olefin feeds was incorporated into the alkylate gasoline products and made the analysis of the alkylate gasoline products more complicated. The alkylation process we employed can make isopentane or n-pentane, and the amount of the synthesized isopentane or n-pentane needed to be differentiated from the corresponding components that came with the olefin feeds. We conducted component material balance around the unit to estimate the amount of isopentane and n-pentane produced by the alkylation process.

The yields of the synthesized hydrocarbon products by the alkylation process are called herein as "true" yields. To calculate the "true" yields of isopentane, n-pentane and $C_6$-$C_{11+}$ carbon product fractions, material balance calculations around the alkylation process unit were conducted. Using the data with >97% material balance closures, the isopentane and n-pentane amounts supplied by the olefin feeds were subtracted from the apparent alkylate gasoline product amounts, and the "true" yields were thus estimated. The "true" yield results are summarized in Table 4.

When the olefin feed contained only 2.2 mol % $C_5$ olefins (97 mol % $C_4$ olefins, Feed #1), the alkylation process made about 9.0 wt % isopentane (Example 3). With Feed #2 containing 14 mol % $C_5$ olefins, the amount of isopentane produced by the alkylation process was about the same as for Feed #1 (9.1 vs. 9.0 wt % isopentane) and the $C_9$ yield was increased from 10.1 to 13.7 wt % (Example 4). The results suggested that the incremental increase in $C_5$ olefins in Feed #2 was converted selectively to $C_9$ alkylate gasoline, without producing any more isopentane than the $C_4$ olefins in Feed #1.

While it was difficult to calculate the isopentane-make from the $C_5$ olefins only for these mixed feeds, by comparing them with the base case, one could roughly estimate the amount of net $C_5$ olefin conversion to isopentane. Since the true isopentane yield of the feed containing 2.2 mol % $C_5$ olefin (Example 3 with Feed #1) and 14.2 mol % $C_5$ olefin (Example 4 with Feed #2) were nearly identical, we could say that only a small portion of the additional $C_5$ olefins in Feed #2 was converted to isopentane, not any more than $C_4$ olefins in the Feed #1. The yield of isopentane from $C_5$ olefins for the Example 4 was estimated to be about 9 wt % or 14 mol %.

As the $C_5$ olefin contents in the olefin feeds were further increased to 39.5 mol %, 59.3 mol % and 75 mol % in Feed #3 through Feed #5, the "true" $C_9$ alkylate gasoline yields were steadily increased from 28.2 wt % to 46.2 wt % (Examples 5 through 7).

For the high $C_5$ olefin containing feeds (Feed #3 through Feed #5), the amount of isopentane in the olefin feeds also increased. Surprisingly, for these same feeds, we observed net decreases of isopentane yields by about 2-10 wt % after the alkylation process (Examples 5 through 7). Apparently some of isopentane in the olefin feeds reacted with olefins to form alkylate gasoline product. The ability of the acidic ionic liquid alkylation catalyst to perform simultaneous

TABLE 4

"True" Yield Estimate of Isopentane and n-Pentane and Carbon Number Distribution

| | Example Number | | | | |
| --- | --- | --- | --- | --- | --- |
| Olefin Feed Source | Example 3 Base Case Alkylate Feed #1 | Example 4 Invention Alkylate Feed #2 | Example 5 Invention Alkylate Feed #3 | Example 6 Invention Alkylate Feed #4 | Example 7 Invention Alkylate Feed #5 |
| Mol % of C5 Olefins/Total Olefins | 2.2 | 14.2 | 39.5 | 59.3 | 75.0 |
| Wt % of Olefins in Olefin Feed | 53.6 | 49.7 | 47.0 | 47.4 | 45.9 |
| Wt % of Isopentane in Olefin Feed | 3.2 | 12.7 | 29.8 | 37.8 | 48.5 |
| nC5 formation/total olefins (mol/mol) | 0.0 | 0.0 | 0.0 | 0.0 | 0.0 |
| iC5 formation/total olefins (mol/mol) | 0.14 | 0.15 | −0.04 | −0.07 | −0.15 |
| mol % of C5= converted to iC5 | Base case | About 14% | 0% | 0% | 0% |
| True Alkylate Yield, wt % | | | | | |
| Isopentane | 9.0 | 9.1 | −2.3 | −4.4 | −9.7 |
| n-pentane | −0.9 | 0.1 | −0.1 | −1.1 | −0.8 |
| C6 | 9.1 | 6.4 | 9.6 | 15.9 | 9.2 |
| C7 | 7.1 | 5.2 | 5.3 | 5.2 | 3.5 |
| C8 | 56.9 | 59.5 | 50.4 | 48.4 | 36.3 |
| C9 | 10.1 | 13.7 | 28.2 | 27.0 | 46.2 |
| C10 | 4.4 | 3.1 | 6.3 | 6.2 | 13.1 |
| C11+ | 4.3 | 3.0 | 2.6 | 2.8 | 2.2 |
| Sum | 100.0 | 100.0 | 100.0 | 100.0 | 100.0 |
| C8 + C9 Selectivity | 67.0 | 73.2 | 78.6 | 75.4 | 82.5 |

The results in Table 4 show that the n-pentane product yield, relative to the total olefin content in the olefin feed, was zero for all of the olefin feeds, indicating that our alkylation process produces negligible amount of n-pentane.

conversion of isobutane and isopentane into high quality alkylate gasoline product appeared to be unique.

For the Examples 5 through 7, there were rather net reductions of isopentane content in the alkylate products. We could clearly say that additional C$_5$ olefins in Feed #3 through 5 were not converted to isopentane, thus the yields of isopentane from C$_5$ olefins for the Examples 5 through 7 were zero.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed. Unless otherwise specified, all percentages are in weight percent.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All of the publications, patents and patent applications cited in this application are herein incorporated by reference in their entirety to the same extent as if the disclosure of each individual publication, patent application or patent was specifically and individually indicated to be incorporated by reference in its entirety.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible subgeneric combinations of the listed components and mixtures thereof.

The invention illustratively disclosed herein suitably may be practiced in the absence of any element which is not specifically disclosed herein.

It is claimed:

1. A process to make an alkylate gasoline, comprising:
   a) providing an alkylation feed, comprising at least 8 wt % total pentenes, from greater than 2 wt % to 10 wt % 1-pentene, a butene, and from 25 wt % to less than 60 wt % isopentane; wherein an amount of the total pentenes in the alkylation feed is from 35 to 99 mol % of a total olefin content in the alkylation feed;
   b) providing an isoparaffin feed comprising isobutene; and
   c) alkylating the alkylation feed with the isoparaffin feed using an acidic ionic liquid alkylation catalyst under alkylation conditions to make the alkylate gasoline; wherein less than 5 mol % of the total pentenes in the alkylation feed are converted to isopentane; wherein an amount of the isopentane in the alkylate gasoline is less than the wt % of the isopentane in the alkylation feed; and wherein the alkylate gasoline has a final boiling point from 370° F. (187.8° C.) to 400° F. (204.4° C.) and a RON of 85 or greater.

2. An alkylation process comprising:
   a) providing an alkylation feed, comprising at least 8 wt % total pentenes, from greater than 2 wt % to 10 wt % 1-pentene, and from 25 wt % to less than 60 wt % isopentane; wherein an amount of the total pentenes in the alkylation feed is from 35 to 99 mol % of a total olefin content in the alkylation feed;
   b) providing an isoparaffin feed comprising isobutene; and
   c) alkylating the alkylation feed with the isoparaffin feed using an acidic ionic liquid alkylation catalyst under alkylation conditions to make an alkylate gasoline; wherein less than 5 mol % of the total pentenes in the alkylation feed are converted to isopentane; wherein an amount of the isopentane in the alkylate gasoline is less than the wt % of the isopentane in the alkylation feed; wherein the alkylate gasoline has a final boiling point from 370° F. (187.8° C.) to 400° F. (204.4° C.) and a RON of 85 or greater; and wherein an n-pentane product yield relative to the total olefin content in the alkylation feed is from zero to less than 0.2 mol/mol.

3. The process of claim 1 or claim 2, wherein the amount of the total pentenes in the alkylation feed is from 35 to 85 mol % of the total olefin content in the alkylation feed.

4. The process of claim 1 or claim 2, wherein the acidic ionic liquid alkylation catalyst conducts simultaneous conversion of both the isobutene in the isoparaffin feed and the isopentane in the alkylation feed to the alkylate gasoline during the alkylating.

5. The process of claim 1 or claim 2, additionally comprising:
   Isolating a stream comprising C$_5$ olefins from a FCC unit to provide the alkylation feed and wherein the alkylating converts the stream comprising C$_5$ olefins to the alkylate gasoline without increasing a throughput of the FCC unit.

6. The process of claim 1 or claim 2, wherein:
   the alkylation feed comprises from 20 wt % to 40 wt % total pentenes and from greater than 25 wt % to 55 wt % isopentane;
   the alkylating converts both the isopentane and the pentenes in the alkylation feed to the alkylate gasoline.

7. The process of claim 1 or claim 2, wherein the alkylating converts 100 wt % of the olefins in the alkylation feed.

8. The process of claim 1 or claim 2, wherein the alkylate gasoline comprises C$_8$ hydrocarbons and wherein an amount of a trimethylpentane in the C$_8$ hydrocarbons is from 70 wt % to 95 wt %.

9. The process of claim 1 or claim 2, wherein the alkylate gasoline comprises C$_9$ hydrocarbons and wherein an amount of a trimethylhexane in the C$_9$ hydrocarbons is from 85 wt % to 95 wt %.

10. The process of claim 1 or claim 2, wherein the alkylate gasoline comprises a C$_{5+}$alkylate fraction having a RVP from 2.3 to 6.0 psi.

11. The process of claim 1 or claim 2, wherein the RON is from 90.0 to 94.5.

12. The process of claim 1 or claim 2, wherein a level of the pentenes in the alkylation feed is increased and does not increase a formation of a conjunct polymer in the acidic ionic liquid alkylation catalyst during the alkylating.

13. The process of claim 1, wherein an n-pentane product yield relative to the total olefin content in the alkylation feed is from zero to less than 0.2 mol/mol.

14. The process of claim 1 or claim 2, additionally comprising selectively hydrogenating a refinery stream comprising olefins to make the alkylation feed, and wherein the alkylation feed comprises from zero to 0.5 wt % dienes.

15. The process of claim 1 or claim 2, additionally comprising selectively hydrogenating the alkylation feed prior to the alkylating.

16. The process of claim 1, wherein the alkylation feed comprises from 20 wt % to 40 wt % total pentenes.

17. The process of claim 1, wherein the alkylation conditions include an alkylation temperature of 20° C. to 100° C.

18. The process of claim 1, wherein the alkylation feed further comprises dienes.

19. The process of claim 1 or claim 2, wherein the amount of the total pentenes in the alkylation feed is from 35 to 75 mol % of the total olefin content in the alkylation feed.

* * * * *